United States Patent [19]

Deschrijver et al.

[11] Patent Number: 4,925,941

[45] Date of Patent: May 15, 1990

[54] PROCESS FOR THE MANUFACTURE OF A 2,3-DIHYDROXYQUINOXALINE, AND 2,3-DIHYDROXYQUINOXALINES THUS OBTAINED

[75] Inventors: Paul Deschrijver, Lennik; Jean-Pierre Ganhy, Brussels, both of Belgium

[73] Assignee: Interox (Sociéte Anonyme), Brussels, Belgium

[21] Appl. No.: 164,463

[22] Filed: Mar. 4, 1988

[30] Foreign Application Priority Data

Mar. 6, 1987 [FR] France .................. 87.03227

[51] Int. Cl.$^5$ .......................... C07D 241/44
[52] U.S. Cl. ..................................... 544/354
[58] Field of Search .......................... 544/354

[56] References Cited

U.S. PATENT DOCUMENTS

| | | | |
|---|---|---|---|
| 3,943,179 | 3/1976 | Bost et al. | 568/771 |
| 4,430,502 | 2/1984 | Nelson | 544/354 |
| 4,628,126 | 12/1986 | Drauz et al. | 568/771 |
| 4,812,458 | 3/1989 | Honore et al. | 544/354 |

OTHER PUBLICATIONS

Kirk-Othmer Encyclopedia of Chemical Technology Third Edition, vol. 20, pp. 591–593 (1982).
Newbold et al., "The Oxidation of 2—hydroxyquinoxaline and its Derivatives with Hydrogen Peroxide", Journal Chemical Society, 1948, pp. 519–522.
Landquist et al., "Derivatives of Py-Hydroxalkyl-, -Aminoalkyl-, and -Carboxy-Quinoxalines", Journal Chemical Society, 1956, pp. 1269–2572.
G. W. H. Cheeseman, "Some 2-Substituted Quinokalines", Journal Chemical Society, 1957, pp. 2845–4156.
Beilstein, Second Supplement, vol. XXIV Syst. No. 3591, pp. 380–381.
Rhone-Poulene, Chemical Abstract, vol. 84, No. 164422z (1976).

Primary Examiner—Anton H. Sutto
Assistant Examiner—F. Bernhardt
Attorney, Agent, or Firm—Spencer & Frank

[57] ABSTRACT

A quinoxaline is oxidized by means of hydrogen peroxide in an inert solvent medium in the presence of water and of a catalyst selected from selenium and selenium compounds.

The process applies to the preparation of substituted and unsubstituted 2,3-dihydroxyquinoxalines.

6 Claims, No Drawings

PROCESS FOR THE MANUFACTURE OF A 2,3-DIHYDROXYQUINOXALINE, AND 2,3-DIHYDROXYQUINOXALINES THUS OBTAINED

The present invention relates to a process for the manufacture of a 2,3-dihydroxyquinoxaline according to which a quinoxaline is oxidized by means of hydrogen peroxide in a solvent medium.

The products obtained by the said process are also included within the scope of the invention.

2,3-Dihydroxyquinoxalines have been known for a long time and find many applications in photography, as insecticides and as polymerization additives for improving polymer properties.

It has long been known that 2,3-dihydroxyquinoxaline may be obtained by reaction of o-phenylenediamine with oxalic acid or with an oxalic acid ester in a hydrochloric acid medium (Beilstein second Supplement, 1954, vol. XXIV, Syst. No. 3591, pages 380-381, in particular, page 380). Furthermore, various methods have been proposed for synthesizing 2,3-dihydroxyquinoxaline by oxidation of substituted quinoxalines by means of hydrogen peroxide in an acetic acid medium (Journal of Chemical Society, 1948, London, G. T. Newbold and F. S. Spring "The oxidation of 2-hydroxyquinoxaline and its Derivatives with Hydrogen Peroxide", pages 519 to 523, in particular, pages 522 and 523; ibid., 1956, London, J. K. Landquist and J. A. Silk "Quinoxaline N-oxides. Part IV. Derivatives of Py-Hydroxyalkyl-, Aminoalkyl-, and -Carboxy-quinoxalines", pages 2052 to 2058, in particular, page 2058; ibid., 1957, London, G. W. H. Cheeseman "Quinoxalines and Related Compounds. Part III. Some 2-Substituted Quinoxalines", pages 3236 to 3239, in particular, page 3238).

However, these known processes do not make it possible to obtain substituted derivatives of 2,3-dihydroxyquinoxaline in good yields. In addition, they present the disadvantage of requiring very long reaction times.

The invention overcomes these disadvantages of the known processes by providing a new process for the manufacture of substituted or unsubstituted 2,3-dihydroxyquinoxalines in which the yields are higher than those of the known processes, with appreciably shorter reaction times.

To this end, the invention relates to a process for the manufacture of a 2,3-dihydroxyquinoxaline by oxidation of a quinoxaline by means of hydrogen peroxide in an inert solvent, according to which the oxidation is performed in the presence of water and of a catalyst selected from selenium and selenium compounds.

The expression 2,3-dihydroxyquinoxalines is intended to denote a compound of general formula:

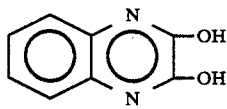

in which the hydrogen atoms of the benzene nucleus may be unsubstituted or substituted.

The quinoxaline employed may be unsubstituted quinoxaline or a quinoxaline substituted on the benzene nucleus. Alternatively, it is possible to use a mixture of several substituted quinoxalines or a mixture of unsubstituted quinoxaline with one or more substituted quinoxalines.

Examples of substituents which are suitable are those which constitute electron-donating groups such as methyl, ethyl, n-propyl or isopropyl groups.

The substituents which constitute electron-acceptor groups are also suitable. Examples of such substituents are halogen, amine or nitro groups. It is also possible to use quinoxalines substituted by more than one substituent. Such polysubstituted quinoxalines may contain one or more electron-donor substituents and one or more electron-acceptor substituents on the benzene nucleus.

According to the invention, the catalyst employed may consist of selenium metal, of selenium oxide, of selenous acid or of selenic acid. It is also possible to employ organic compounds of selenium, particularly organoselenium compounds. It has been found that the use of selenium oxide is particularly advantageous.

In most cases, the catalyst is employed in a concentration of between 9 and 150 millimoles per mole of quinoxaline. In order to avoid the formation of an excessive quantity of monooxyquinoxaline, it is preferable to employ more than 25 millimoles of catalyst per mole of quinoxaline. Similarly, in order to limit the formation of dioxyquinoxaline, it is preferable not to exceed a concentration of 80 millimoles of catalyst per mole of quinoxaline. The catalyst may be incorporated in the reaction medium in the pure state, in solution or as a dispersion in a solvent.

The hydrogen peroxide used to oxidize the quinoxalines according to the process of the invention may be employed in the anhydrous state, in the form of a commercial aqueous solution or in the form of a solution in an organic solvent. Aqueous solutions are generally preferred because of their lower cost and their greater availability. Aqueous solutions containing at least 10% by weight and not more than 95% by weight of hydrogen peroxide are suitable. Solutions which contain between 20 and 90% by weight of hydrogen peroxide are preferably employed.

The purpose of the inert solvent in the process according to the invention is to form a homogeneous liquid medium capable, under the reaction conditions, of dissolving the quinoxaline, the hydrogen peroxide and the 2,3-dihydroxyquinoxaline formed. It should be inert towards the quinoxaline employed, to hydrogen peroxide and to the oxidation products. It may be an organic solvent which is resistant to oxidation by hydrogen peroxide under the reaction conditions or a mixture of one or more of these solvents with a quantity of water such that the weight proportion of water to solvent is between 0 and 0.4. The most advantageous organic solvents are those chosen from aliphatic alcohols, cyclohexanol, benzyl alcohol and dioxan. Ethanol, n-propanol, n-butanol and polyethylene glycol are particularly suitable.

The quantity of inert solvent to be employed is not critical. It depends on various factors such as the nature of the quinoxaline, the concentration of the hydrogen peroxide solution, the solubility of the 2,3-dihydroxyquinoxaline in the reaction mixture and the technique for extracting it from this mixture. It can be determined in each case in question by means of a limited number of laboratory tests. The weight quantity of solvent is generally between 2 and 50 times the weight of quinoxaline employed. In most cases, this weight of solvent is more than 4 times the weight of quinoxaline and does not exceed 20 times this weight. A weight of solvent of between 8 and 12 times the weight of quinoxaline employed is particularly suitable.

According to the invention, oxidation of the quinoxaline by hydrogen peroxide should be carried out in the presence of water. The latter may consist essentially of the water produced during the reaction. Alternatively, it may comprise an excess of water relative to that originating from the oxidation reaction; this excess of water may, for example, accompany the inert solvent and/or the hydrogen peroxide when the latter is employed in the form of an aqueous solution. As a general rule, it has been found desirable to use a weight excess of water of at least 1% of the weight of the inert solvent, but preferably not exceeding 50% of this weight. Weight excesses of water of between 5 and 35% of the weight of inert solvent are preferred.

The temperature and the pressure at which the oxidation reaction according to the invention is carried out are not critical and may vary within wide limits. They depend on the nature of the quinoxaline to be oxidized and that of the inert solvent. They also affect the reaction time and need to be determined for each particular case by means of routine laboratory tests.

The reaction time depends on the nature of the quinoxaline to be oxidized and of the catalyst and of the solvent employed. It may vary between 2 and 25 hours, depending on the temperature.

After reaction, the mixture may be subjected to various separation techniques such as distillation, phase separation and filtration in order to recover the 2,3-dihydroxyquinoxaline formed and the unconverted reactants. In a particular embodiment of the invention, the unconverted reactants are recovered at the end of the separation operation. They may then be advantageously recycled into the process.

The process according to the invention may be carried out continuously or noncontinuously, in a single reactor or in a series of reactors in parallel or in series, of the usual types which are suitable for liquid reaction mixtures.

The catalyst and the reactants may be introduced in various manners known per se. Thus, according to the case in question, the catalyst, the quinoxaline and/or the hydrogen peroxide may be introduced in stages, or all these constituents may be mixed simultaneously.

The process according to the invention offers the advantage of providing substituted or unsubstituted 2,3-dihydroxyquinoxalines in yields which are better than those obtained with the known processes.

In order to illustrate the invention, without, however, limiting its scope, examples of manufacture of 2,3-dihydroxyquinoxalines (Examples 1 to 4 and Example 7) by means of the process according to the invention are given below. Examples 5R, 6R and 8R relate to reference tests, not according to the invention.

EXAMPLES 1 TO 6R 200 mg (1.8 millimoles) of $SeO_2$, 50 ml of solvent and 6.5 g (50 millimoles) of quinoxaline were introduced into a jacketed reactor fitted with an internal cooling system, a magnetic stirrer and a device for introducing a liquid reactant.

The temperature of the mixture was then taken to 70° C. and 6 ml of an aqueous solution of $H_2O_2$ at a concentration of 85% by weight (200 millimoles) were then introduced over 1 minute via the device for introducing a liquid reactant. After several minutes, a brown precipitate formed. After reaction had been allowed to proceed for a sufficient time, the reaction was stopped by cooling the reaction mixture.

The reaction products were then analyzed in the precipitate (by nuclear magnetic resonance and thin layer chromatography) and in the filtrate (by thin layer chromatography).

Tests 1 to 4 were carried out in accordance with the invention, without removing water from the reaction mixture. In test 1, the solvent consisted of anhydrous n-propanol. In tests 2, 3 and 4, a mixture of n-propanol and water was employed as an inert solvent in order to deliberately increase the water content of the reaction mixture.

Test 5R was carried out by way of comparison with water being continuously removed from the reaction mixture by the use of a Florentine phase-separator at the bottom of the condenser.

Test 6R was carried out without catalyst, by way of reference.

The results of the analyses together with the reaction time and solvent composition are given in Table I, which follows.

The references DHQ, MOQ and DOQ denote 2,3-dihydroxyquinoxalines, monooxyquinoxalines and dioxyquinoxalines, respectively.

The last column of Table I shows whether the analysis has been carried out on the filtrate (reference F) or on the precipitate (reference P). Opposite reference T, Table I also gives the sum total of the results obtained from the filtrate and from the precipitate.

TABLE I

| Example No. | Reaction time, h | Weight ratio solvent/water | Molar yield, % | | | |
|---|---|---|---|---|---|---|
| | | | DHQ | MOQ | DOQ | |
| 1 | 17 | 100:0 | 5.0 | 17.8 | 13.6 | F |
| | | | 19.5 | 0.2 | 0.1 | P |
| | | | 24.5 | 35.8 | 27.4 | T |
| 2 | 17 | 95:5 | 7.4 | 38.4 | 19.8 | F |
| | | | 22.0 | 0.4 | 0.2 | P |
| | | | 29.4 | 38.8 | 20.0 | T |
| 3 | 17 | 90:10 | 7.4 | 41.0 | 9.8 | F |
| | | | 22.6 | 0.8 | 0.2 | P |
| | | | 30.0 | 41.8 | 10.2 | T |
| 4 | 17 | 75:25 | 9.8 | 41.0 | 9.8 | F |
| | | | 15.2 | 0.0 | 0.0 | P |
| | | | 25.0 | 41.0 | 9.8 | T |
| 5R | 2 | 100:0 | 4.2 | 30.2 | 6.6 | F |
| | | | 4.4 | 4.0 | 18.8 | P |
| | | | 8.6 | 34.2 | 25.4 | T |
| 6R | 17 | 100:0 | 0.2 | 16.8 | 0.0 | F |
| | | | 0.0 | 0.0 | 0.0 | P |
| | | | 0.2 | 16.8 | 0.0 | T |

Comparison of the results of Example 1 with those of Examples 5R and 6R shows the advantage of the process according to the invention insofar as the molar yield of 2,3-dihydroxyquinoxaline which is obtained is concerned.

Examples 2 to 4 demonstrate the advantage of introducing an additional quantity of water with the starting materials into the reaction medium.

EXAMPLES 7 AND 8R

Examples 7 and 8R have been carried out under the same conditions as Examples 1 to 5R, except for the nature of the inert solvent, which was replaced with n-butanol.

The results are given in Table II, which follows.

TABLE II

| Example No. | Reaction time, h | Weight ratio solvent/water | Molar yield, % | | | |
|---|---|---|---|---|---|---|
| | | | DHQ | MOQ | DOQ | |
| 7 | 17 | 100:0 | 4.4 | 20.5 | 7.4 | F |
| | | | 6.4 | 1.8 | 45.6 | P |
| | | | 10.8 | 22.3 | 53.0 | T |
| 8R | 17 | 100:0 | 2.2 | 10.3 | 3.7 | F |
| | | | 3.2 | 0.9 | 22.8 | P |
| | | | 5.4 | 11.2 | 26.5 | T |

We claim:

1. A process for the manufacture of a 2,3-dihydroxyquinoxaline by oxidation of an unsubstituted quinoxaline or a quinoxaline substituted on the benzene nucleus at positions 5, 6, 7, and 8 by means of hydrogen peroxide in an inert solvent, wherein the oxidation is performed in the presence of water and a catalyst consisting of selenium oxide.

2. Process according to claim 1, characterized in that the catalyst is employed in a quantity of between 25 and 80 millimoles per mole of quinoxaline.

3. The process according to any one of the preceding claims, wherein the inert solvent is chosen from aliphatic alcohols, cyclohexanol, benzyl alcohol and dioxan.

4. The process according to claim 3, wherein the aliphatic alcohol is chosen from ethanol, n-propanol, n-butanol and polyethylene glycol.

5. The process according to claim 1, wherein at least part of the water employed is the water produced by the oxidation reaction.

6. The process according to claim 1, wherein a quantity of water not exceeding 35% of the weight of the inert solvent is added to the reaction mixture.

* * * * *